(12) United States Patent
Delay

(10) Patent No.: US 7,011,635 B1
(45) Date of Patent: Mar. 14, 2006

(54) MANUAL CONTROL DEVICE FOR A SURGICAL GUIDE

(75) Inventor: Jean-Pascal Delay, Ecully (FR)

(73) Assignee: SEDAT, Irigny (FR)

( * ) Notice: Subject to any disclaimer, the term of this patent is extended or adjusted under 35 U.S.C. 154(b) by 447 days.

(21) Appl. No.: 09/890,577

(22) PCT Filed: Nov. 6, 2000

(86) PCT No.: PCT/FR00/03083

§ 371 (c)(1),
(2), (4) Date: Aug. 2, 2001

(87) PCT Pub. No.: WO01/41860

PCT Pub. Date: Jun. 14, 2001

(30) Foreign Application Priority Data

Dec. 10, 1999 (FR) ................................. 99 15629

(51) Int. Cl.
*A61B 5/00* (2006.01)
*A61M 25/00* (2006.01)
(52) U.S. Cl. ........................ 600/585; 604/523; 604/528
(58) Field of Classification Search ................ 600/433, 600/434, 585; 604/95.01, 103.03, 103.04, 604/164.13, 166.01, 264, 523, 528, 533; 606/139; 251/4, 5, 6, 7, 8, 9, 10
See application file for complete search history.

(56) References Cited

U.S. PATENT DOCUMENTS

| 4,429,852 A | * | 2/1984 | Tersteegen et al. ............ 251/9 |
| 4,716,757 A | * | 1/1988 | McGregor et al. ............ 72/387 |
| 4,829,999 A |   | 5/1989 | Auth |
| 4,973,329 A |   | 11/1990 | Park et al. |
| 5,325,868 A | * | 7/1994 | Kimmelstiel ................ 600/585 |
| 5,423,331 A | * | 6/1995 | Wysham ..................... 600/585 |
| 6,030,349 A | * | 2/2000 | Wilson et al. .............. 600/585 |

FOREIGN PATENT DOCUMENTS

| WO | WO 97 11736 | 4/1997 |
| WO | WO 97 18850 | 5/1997 |

OTHER PUBLICATIONS

Merriam-Webster's Collegiate Dictionary, 2001, Merriam-Webster, Incorporated, 10th ed, 606.*

* cited by examiner

*Primary Examiner*—Max F. Hindenburg
*Assistant Examiner*—Jonathan Foreman
(74) *Attorney, Agent, or Firm*—Sughrue Mion, PLLC

(57) ABSTRACT

The device (10) for manual control of a surgical guide (G) comprises a body (12) provided with a conduit (14) for passage of the surgical guide (G), and a member (16) for axially immobilizing the surgical guide relative to the body. The member (16) is displaceable between a position in which it immobilizes the surgical guide and a position in which it releases the surgical guide. Said immobilizing member (16) is made integral with the body (12).

1 Claim, 4 Drawing Sheets

MANUAL CONTROL DEVICE FOR A SURGICAL GUIDE

BACKGROUND OF THE INVENTION

The present invention relates to a device for manual control of a surgical guide, of the type comprising a body provided with a conduit for passage of the surgical guide, and a member for axially immobilizing the surgical guide relative to the body, which member is displaceable between a position in which it immobilizes the surgical guide and a position in which it releases the surgical guide.

Such a manual control device is used to facilitate handling of a guide inserted during angioplasty and angiography interventions. Such a guide consists of a flexible wire of considerable length, which can be as much as two meters. This guide has a very small diameter, generally between 0.01 inch and 0.045 inch (0.25 mm to 1.15 mm).

During an intervention, the manual control device mounted on the guide allows the guide to be pushed, pulled and turned about itself after its end has been introduced into the human body and in particular into the inside of a vascular conduit.

Displacement of the guide is facilitated because the manual control device constitutes a member which is integral with the guide and whose dimensions make it easy to hold compared with direct action on the guide which is too fine to be easily gripped.

Devices for manual control of guides are already known and are in common use. They comprise a body though which there passes a conduit for passage of the guide. An immobilizing member is engaged about the guide. It is adapted to be screwed onto the body, radially compressing the guide, thereby ensuring that the guide is secured relative to the body.

Such a device is relatively complex and expensive to produce since it includes several components and these components have to be adjusted with precision in order to permit effective screwing.

Manual control devices are also known comprising a body on which an immobilizing member slides and ensures immobilization of the surgical guide by a wedging effect. To immobilize the guide, the immobilizing member is stressed by a ramp forming a cam provided on the body.

This device is also complex to produce since it requires the use of several components and means for precision guiding of the elements relative to one another if it is to be able to function in a satisfactory way.

Moreover, these devices are relatively awkward for the surgeon to manoeuvre since releasing the surgical guide and immobilizing it are not easy.

SUMMARY OF THE INVENTION

It is an object of the invention to make available a device for manual control of a surgical guide which is inexpensive to produce and easy to use.

To this end, the subject of the invention is a device for manual control of a surgical guide, of the aforementioned type, characterized in that said immobilizing member is made integral with the body.

According to specific embodiments, the manual control device includes one or more of the following characteristics:

said immobilizing member comprises a span for transverse bearing on the surgical guide and means for stressing said bearing surface transversely with respect to the axis of the conduit formed in the body;

said stressing means comprise means for elastic return of the immobilizing member to its immobilizing position;

the immobilizing member comprises a conduit for receiving the guide, and the span for transverse bearing on the guide is defined on the surface of said conduit;

said body comprises a seat for receiving the immobilizing member in the immobilizing position, which seat forms an interruption of the conduit, which conduit delimits, on each side of the seat, two spans for transverse bearing of the surgical guide;

it comprises an arm bearing said immobilizing member, which arm is articulated relative to the body; and the arm bearing the immobilizing member is connected to the body via an elastically deformable connecting region constituting said means for elastic return of the immobilizing member to its immobilizing position.

BRIEF DESCRIPTION OF THE DRAWINGS

The invention will be better understood on reading the following description which is given solely by way of example and in which reference is made to the attached drawings, in which.

DETAILED DESCRIPTION OF THE INVENTION

Figure 1:
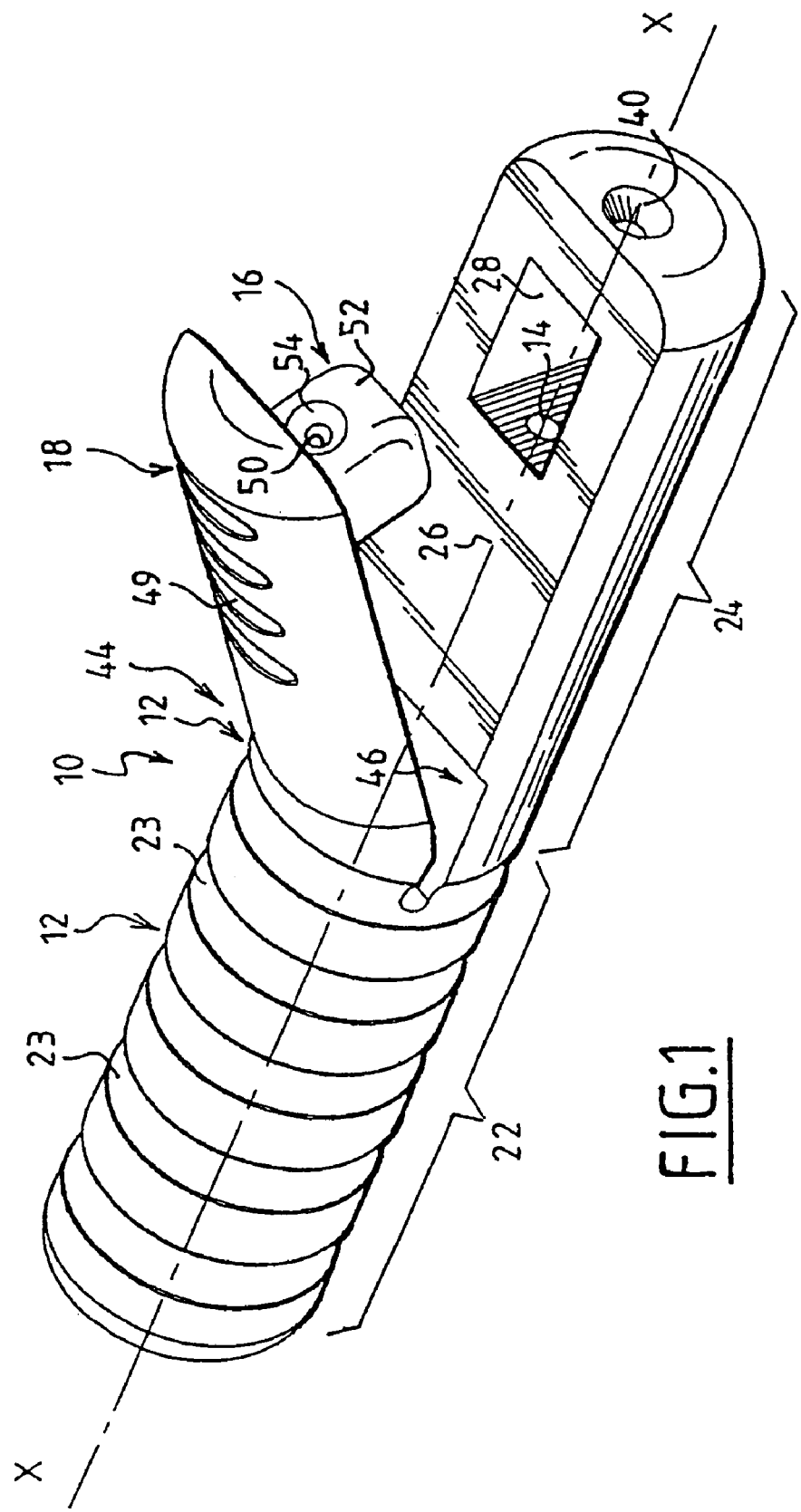
FIG. 1 is a perspective three-quarter view of a manual control device according to the invention, shown on its own.

The device 10 according to the invention, represented in the figures, is intended for manual control of a surgical guide. It has an generally elongate and substantially cylindrical shape with an axis X—X. It has, on the one hand, a body 12 through which a conduit 14 passes axially, and, on the other hand, a member 16 for immobilizing the surgical guide relative to the body. This member 16 is made integral with a control arm 18, itself made integral with the body 12.

More precisely, the body 12 comprises a grip portion 22 on the outside surface of which there are grooves 23 which make it easier to manoeuvre the device.

The grip portion 22 is continued by a portion 24 for immobilizing the surgical guide. This portion of substantially cylindrical outer shape has, along its whole length, a flat surface 26 opposite the arm 18.

The portion 24 comprises a seat 28 for receiving the immobilizing member 16. The seat 28 opens through the flat surface 26 and passes transversely through the immobilizing portion 24. It is delimited by four plane surfaces perpendicular to each other. The seat 28 is formed near the free end of the portion 24.

The conduit 14 extends the whole length of the body. It comprises a main portion 32 extending the whole length of the grip portion 22. It is continued in the immobilizing portion 24 and opens perpendicularly on a lateral face of the seat 28. This main portion is completed by a secondary portion 34 formed between the free end of the immobilizing portion 24 and the seat 28. The conduit 14 has, on each side of the seat 28, portions 36, 38 of reduced cross section.

These portions have a diameter very slightly greater than the diameter of the guide intended to be held there.

In addition, at its ends opening out at the ends of the body 12, the conduit 14 has portions progressively increasing in cross section towards the outside and forming centring cones 40, 42 which make it easier to insert the surgical guide.

As is illustrated in the figures, the arm 18 and the immobilizing member 16 are both made integral with the body 12. Therefore, the manual control device is made by injection-moulding of plastic, in a single operation, in a suitably shaped mould.

The arm 18 is connected to the body 12 via a connecting region 44 forming a hinge which is elastically deformable. In order to facilitate the deformation of the region 44, a clearance 46 is provided in the flat surface 26 opposite the connecting region 44.

The arm 18 has a length substantially equal to that of the immobilizing portion 24. It has a generally cylindrical outer surface and a plane surface 48 arranged opposite the flat surface 26. On its outer surface it has recessed profiles 49 making it easier to act manually on the arm.

At rest, that is to say in the absence of any stress, the arm 18 is spaced apart from the body and defines with the flat surface 26 an angle substantially equal to 300. In this position, the immobilizing member 16 is outside the seat 28. This position of the arm corresponds to the configuration in which the control device is moulded.

The immobilizing member 16 protrudes from the plane surface 48 of the arm. It is arranged near the free end of the arm, opposite the seat 28. It has dimensions such that it can be received in this seat.

The immobilizing member 16 has a substantially parallelepipedal form, its transverse edges being rounded.

Moreover, the member 16 has a conduit 50 passing through it along the axis of the arm, which conduit 50 opens out along transverse faces 52. This conduit 50 has a diameter substantially equal to that of the portions of reduced cross section 36 and 38 of the conduit passing through the body. At its end oriented towards the free end of the arm, the conduit 50 is provided with a centring cone 54 facilitating introduction of the surgical guide.

Figure 3:
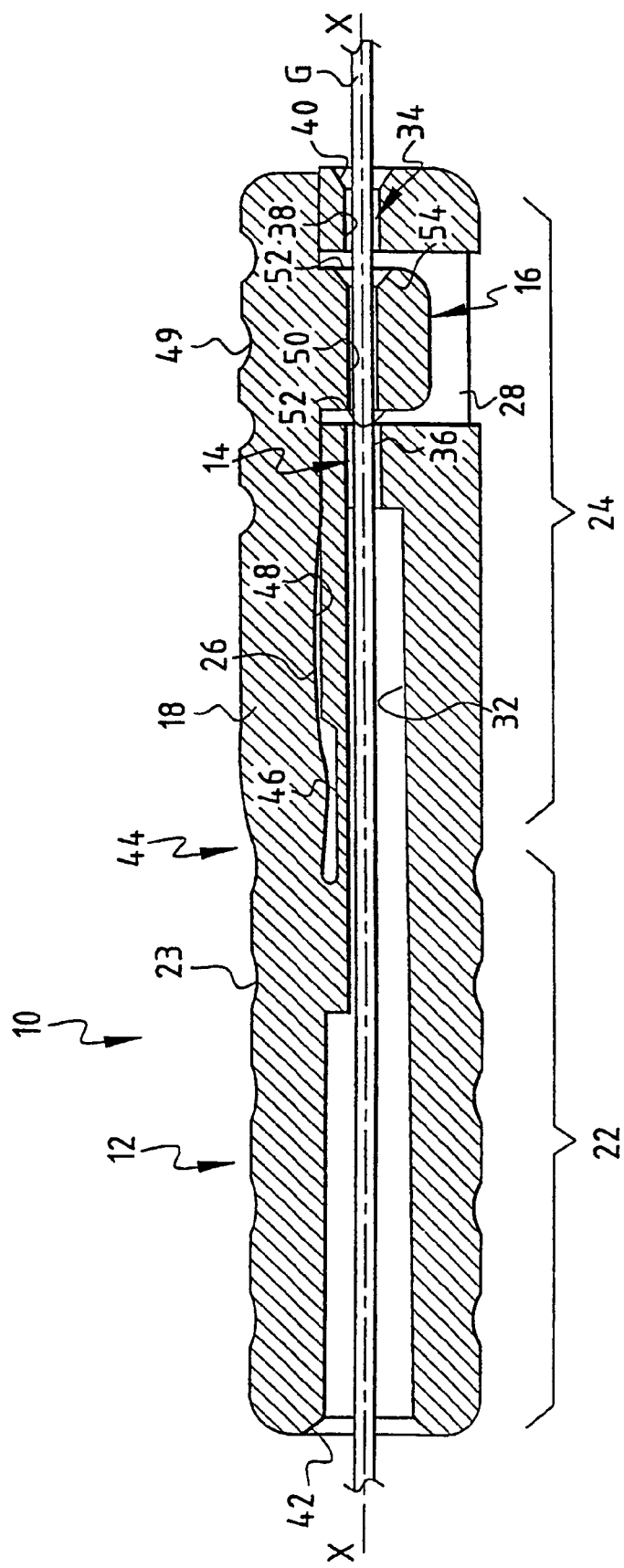
FIG. 3 is a longitudinal cross section through the manual control device in its position in which the surgical guide is introduced or released.

The conduit 50 is formed in a position which is such that when the arm 18 is stressed towards the body and the connecting region 44 is deformed so that the arm 18 bears on the flat surface 26, the conduit 50 and the portions 36 and 38 of the conduit 14 are substantially coaxial, as is illustrated in FIG. 3.

When the arm 18 is bearing on the flat surface 26, the immobilizing member 16 is situated in a position of introduction of the surgical guide labelled G, or in a position of release of the guide, which permits axial displacement and rotational displacement of the control device relative to the surgical guide.

The manual control device represented in the figures is used in the following way.

Figure 2:
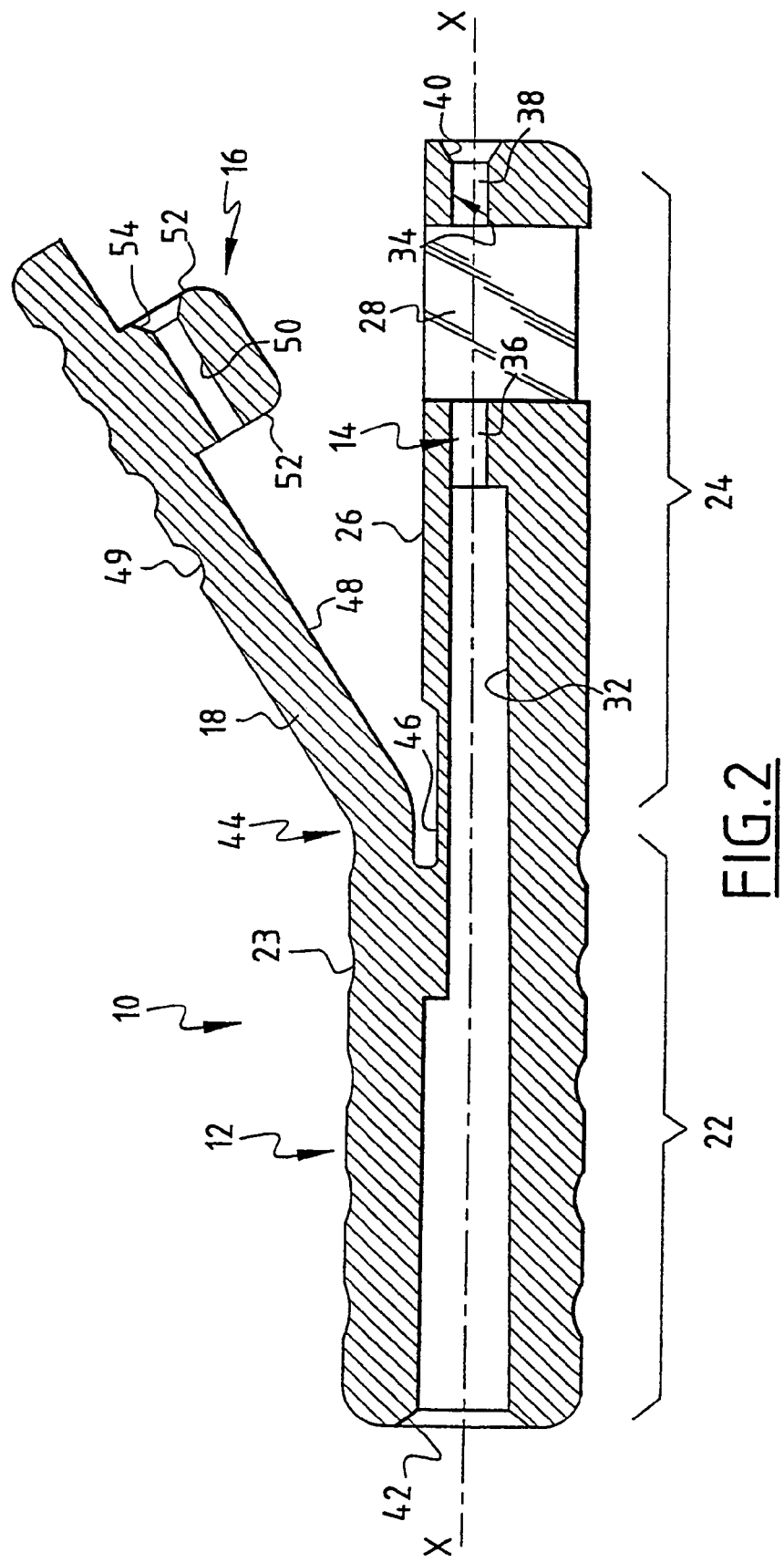
FIG. 2 is a longitudinal cross section through the device from FIG. 1, at rest, and in the absence of a surgical guide.

Initially, the device is in its rest configuration illustrated in FIG. 2.

In order to permit introduction of the surgical guide, the immobilizing member 16 is brought into its position of release of the surgical guide, as is illustrated in FIG. 3, in which the conduit 50 is coaxial with the portions 36 and 38.

For this purpose, the connecting region 44 of the arm is then elastically deformed by manual pressure on the arm 18 until the latter bears against the immobilizing portion of the body.

The surgical guide can then be introduced through the conduit 14. This introduction is advantageously effected via the opening formed at the free end of the immobilizing portion 24.

Figure 4:
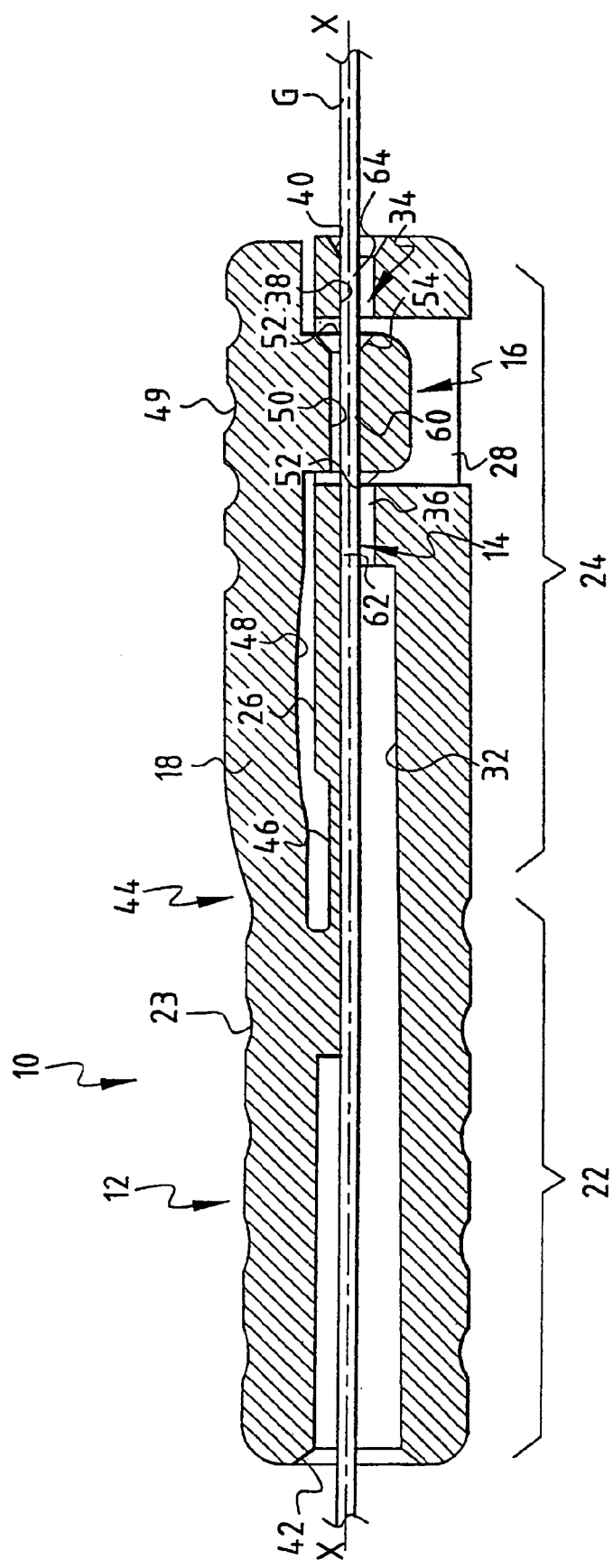
FIG. 4 is a longitudinal cross section through the manual control device according to the invention, in the position in which a surgical guide is immobilized.

After the manual control device has been put in place around the surgical guide in the desired region, the pressure exerted on the arm 18 is interrupted. Thus, under the effect of relaxation of the previously deformed connecting region 44, the arm 18 is returned elastically to its rest position. The immobilizing member 16 then stresses the surgical guide G transversely. Thus, a span, labelled 60 in FIG. 4, of the lateral surface of the conduit 50 stresses the surgical guide G transversely. This span 60 is formed by that region of the conduit 50 which is remote from the arm 18 and is facing towards it.

By contrast, spans labelled 62 and 64 on the portions 36 and 38 and arranged on the side towards the arm 18 constitute bearing surfaces for the surgical guide G. Thus, under the action of the transverse force of elastic return, the surgical guide G is immobilized on the one hand between the spans 60 and 62 and on the other hand between the spans 60 and 64. On account of this immobilization, the surgical guide is immobilized both axially and in rotation relative to the control device.

In this immobilizing position occupied by the member 16, the conduit 50 and the portions 36 and 38 are not in alignment.

The surgical guide G can thus be easily manipulated by the surgeon who holds the control device between his fingers, without bearing on the arm 18.

When the surgeon wishes to slide the manual control device along the guide, or to angularly displace the control device relative to the guide, he manually exerts a bearing force on the arm 18 in such a way as to bring the immobilizing member 16 into its release position illustrated in FIG. 3. The alignment of the conduit 50 and of the portions 36 and 38 ends the wedging of the guide G, and the latter is then free to be displaced.

The presence of the spans 62 and 64 on each side of the immobilizing member 16 ensures a distribution of the forces of sectioning of the surgical guide in two regions along the length thereof, these regions being formed on either side of the member 16. Thus, the mechanical damage to the guide is reduced.

Moreover, the presence of the two spans 62, 64 avoids creating local deformations of the surgical guide, the latter remaining substantially rectilinear in its wedging region.

However, such wedging could also be obtained by omitting one of the portions 36 and 38, the guide G then being immobilized only between a pair of opposite spans 60, 62 or 60, 64.

Likewise, the conduit 50 can be replaced by any profile permitting passage of the guide G and delimiting at least one span for transverse bearing on the guide, and this surface can be plane, for example.

It will be appreciated that the use of the manual control device described here, which is made in one piece since the immobilizing member 16 is made integral with the body, reduces the production cost of the device and increases its reliability. Moreover, manipulation of the device is extremely simple, the surgical guide being automatically immobilized relative to the body by the elastic return exerted on the immobilizing member 16 via the deformable region ensuring connection of the arm 18.

The surgical guide is also released in a very simple way since it suffices to exert a manual pressure on the arm 18 transversely to the surgical guide. Such bearing on the arm

18 is natural to the surgeon, in contrast to the screwing of an immobilizing member or axial displacement thereof relative to the body, both of which necessitate considerable dexterity.

With the device described here, the pressure exerted by the immobilizing member on the surgical guide is fixed by the initial elastic deformation of the arm 18. This pressure is therefore constant and does not depend on the force applied by the surgeon, in contrast to the devices of the prior art where the screwing force or wedging force by axial displacement of a button depend on the action of the surgeon. Thus, any risk of poor immobilization as a result of an insufficient wedging force or of damage to the guide by an excessive wedging force is avoided, the wedging force being defined by the constant force of elastic return of the arm.

What is claimed is:

1. Device (10) for manual control of a surgical guide (G), comprising a body (12) provided with a conduit (14) for passage of the surgical guide (G), and a member (16) for axially immobilizing the surgical guide relative to the body, which member (16) comprises a conduit (50) for receiving the surgical guide and is displaceable between a position in which it immobilizes the surgical guide and in which the conduits (14, 50) formed in the body (12) and in the immobilizing member (16) are not aligned, and a position in which it releases the surgical guide and in which the conduits (14, 50) formed in the body (12) and in the immobilizing member (16) are aligned, the device comprising means (44) for elastic return of the immobilizing member (16) to its immobilizing position, characterized in that:

said immobilizing member (16) is made integral in one piece with the body (12);

said body (12) comprises a seat (28) for receiving the immobilizing member (16) in the immobilizing position, which seat (28) forms an interruption of the body conduit (14), which body conduit (14) delimits, on each side of the seat (28), two spans (62, 64) for transverse support of the surgical guide (G);

at rest, the immobilizing member (16) is outside the seat (28) provided for receiving the immobilizing member;

said device comprises an arm (18) bearing said immobilizing member (16), which arm (18) is articulated relative to the body (12); and the arm (18) bearing the immobilizing member is connected to the body (12) via an elastically deformable connecting region (44) constituting said means for elastic return of the immobilizing member (16) to its immobilizing position.

\* \* \* \* \*